(12) United States Patent
Zimmerman

(10) Patent No.: US 7,189,960 B2
(45) Date of Patent: Mar. 13, 2007

(54) OPTICAL MOISTURE SENSOR

(75) Inventor: James Zimmerman, Walnut, CA (US)

(73) Assignee: The Toro Company, Bloomington, MN (US)

(*) Notice: Subject to any disclaimer, the term of this patent is extended or adjusted under 35 U.S.C. 154(b) by 32 days.

(21) Appl. No.: 11/214,100

(22) Filed: Aug. 29, 2005

(65) Prior Publication Data

US 2006/0043269 A1    Mar. 2, 2006

Related U.S. Application Data

(60) Provisional application No. 60/605,004, filed on Aug. 27, 2004.

(51) Int. Cl.
*G01N 21/01* (2006.01)
*G01J 31/10* (2006.01)

(52) U.S. Cl. ............... 250/227.25; 250/573; 356/128; 340/603

(58) Field of Classification Search ........... 250/216, 250/227.25, 573, 574; 356/128–137, 436; 340/603, 604, 606, 618, 619
See application file for complete search history.

(56) References Cited

U.S. PATENT DOCUMENTS 2,866,379 A  * 12/1958  Veit .......................... 250/575
3,751,173 A  *  8/1973  Sanz et al. ................. 356/246
3,787,703 A  *  1/1974  Topol ......................... 250/574
3,900,396 A  *  8/1975  Lamadrid ..................... 210/94
4,430,646 A  *  2/1984  Enemark ..................... 340/630
4,823,168 A  *  4/1989  Kamahori et al. .......... 356/246
4,922,433 A       5/1990  Mark
5,445,178 A       8/1995  Feuer
5,749,521 A       5/1998  Lattery
5,813,606 A       9/1998  Ziff
6,073,427 A       6/2000  Nichols
6,254,828 B1 *   7/2001  LaCount ...................... 422/78
6,784,988 B2 *   8/2004  Vijayakumar et al. ...... 356/244
6,947,132 B1     9/2005  Boss et al.
2004/0100394 A1  5/2004  Hitt

FOREIGN PATENT DOCUMENTS

EP          126031 A2 *  11/1984

* cited by examiner

*Primary Examiner*—Stephone B. Allen
(74) *Attorney, Agent, or Firm*—Inskeep IP Group, Inc.

(57) ABSTRACT

A soil moisture sensor has a cylindrical body of transparent cyclic olefin polymer (COC). A pair of axially spaced cavities tapered toward each other are formed in the body. A light source is placed in one of the cavities, and a light sensor is placed in the other. The walls of the cavities are so curved that divergent light rays from the light source are refracted at the cavity-body interface into parallelism, and that reflected parallel rays are refracted at the body-cavity interface so as to focus on the light sensor. The parallel rays coming from the light source are reflected or refracted at the outer surface of the body, depending upon whether the ambient environment of the sensor is dry or wet.

10 Claims, 3 Drawing Sheets

OPTICAL MOISTURE SENSOR

RELATED APPLICATIONS

This application claims priority to U.S. Provisional Application Ser. No. 60/605,004 filed Aug. 27, 2004 entitled Optical Moisture Sensor and is hereby incorporated by reference.

FIELD OF THE INVENTION

This invention relates to optical moisture sensors for irrigation systems, and more particularly to an elongated, preferably cylindrical sensor using internal refraction to convert infrared radiation from a point source into parallel rays which are reflected from, and/or refracted at, the outer surface of the sensor in accordance with the moisture level at that surface, the reflected rays being then refocused by internal refraction onto a point light receiver.

BACKGROUND OF THE INVENTION

Optical sensors for determining the moisture content of the soil in an irrigation system are well known. They usually take the form of a prism or similar structure, in which a light beam projected into the prism is internally reflected toward a light sensor, e.g. a photodiode. The amount of light received by the light sensor depends on the amount of moisture present at the surfaces of the prism. This moisture changes the optical characteristics of the prism surface and thereby causes a portion of the beam to be refracted outwardly of the prism, instead of being reflected inwardly toward the light sensor. The amount of refraction, and thus the amount of light received by the light sensor, translates into a measurement of the wetness of the soil.

Typical examples of the prior art are illustrated in U.S. Pat. No. 5,946,084 to Kubulins (a dome-shaped structure) and U.S. Pat. No. 6,079,433 to Saarem (a flat-surface prism). These devices are useful, but they are of limited efficiency because they rely on the reflection of divergent beams of light and are not readily suitable for miniaturization. Also, double-reflection devices of the prior art significantly limit the surface available for sensing and can only use a small arc of the illumination provided by the light source.

SUMMARY OF THE INVENTION

The present invention provides a highly efficient, miniaturizable optical moisture sensor in the form of an elongated, preferably cylindrical body of transparent plastic material such as a cyclic olefin copolymer (COC) commonly used in medical-grade optical instruments. The body has formed therein two tapered, axially spaced air-filled cavities that are coaxial with the body and face each other. One of the cavities contains an infrared source, the other a phototransistor. The size of the cavities is such that the infrared source and phototransistor can be considered focal points for practical purposes. The tapered walls of the cavities are curved in such a manner that divergent rays from the infrared source are refracted at the air-COC interface into parallelism with each other. The parallel rays form an angle with the outer surface of the body that is approximately half way between the critical angle for reflection at the body surface when the body is immersed in water, and the critical angle for reflection when the body is dry.

The axial spacing of the cavities and the curvature of the tapered wall of the phototransistor cavity is such that, through a wide arc of illumination, any parallel rays reflected from the body surface are refracted at the phototransistor cavity's COC-air interface into a focus at the phototransistor. Thus, the sensor structure of this invention assures that essentially the only loss of infrared energy between the infrared source and the phototransistor (within the limits of the useful illumination arc) is the optical energy that is refracted outside the body due to the presence of moisture at the body surface.

DESCRIPTION OF THE PREFERRED EMBODIMENT

Figure 1:
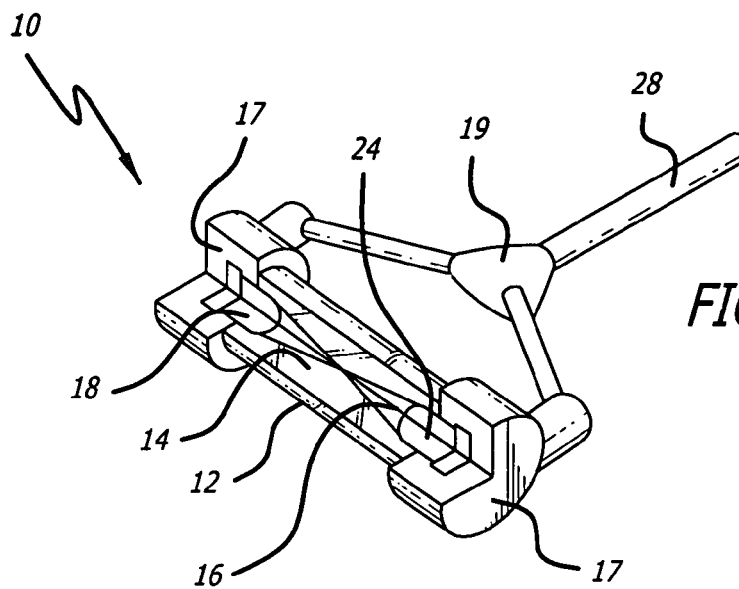
FIG. 1 is a partially cut-away perspective view of a preferred embodiment of the sensor unit of this invention.

As shown in FIG. 1, the moisture sensor 10 of this invention consists of an elongated body 12 formed from a transparent plastic material such as cyclic olefin copolymer (COC). COC is a preferred material because of its low moisture absorption. A cylindrical shape is preferred for the body 12 because that configuration permits the use of standard infrared emitting diodes (IREDs) and phototransistors. It also minimizes potentially troublesome internal air volume, and reduces many parts to one. This results in much simpler tooling, makes the sensor 10 very compact for a given effective sensing area, and provides a surface that makes orientation of the sensor non-critical.

The body 12 has a pair of tapered cavities 14, 16 formed therein. A light source such as an IRED 18 is mounted in the cavity 14 at a predetermined point on the axis A (FIG. 2) of the cylinder 12. A plug 15, preferably also made of COC, is formed at the base of the IRED 18 to close off the entrance to the cavity 14. The plug 15 is secured to the body 12 by an appropriate moisture-proof adhesive to form a moisture-proof seal. A close fit between the plug 15 and the body 12, as well as the forming of plug 15 around the IRED power wires 22, assures the minimization of any migration path through which moisture could reach the interior of cavity 14.

Likewise, a light receiver such as a phototransistor 24 is mounted in the cavity 16 at a predetermined point on the axis A of the cylinder 12. The cavity 16 is then also sealed, as described above, by a plug 25 to prevent penetration of moisture into the cavity 16, or migration of moisture along the wires 26 that carry the signal generated by the photodiode 24. In a preferred embodiment, the wires 22 and 26 are then encapsulated in a suitable flexible or hard material 17 to form a wiring yoke joined at 19 to form a cable 28 for connection to a watering control system (not shown). In operation, the moisture sensor 10 is buried in the soil to be irrigated. Its orientation is essentially immaterial, although a horizontal position is usually preferred.

Figure 2:
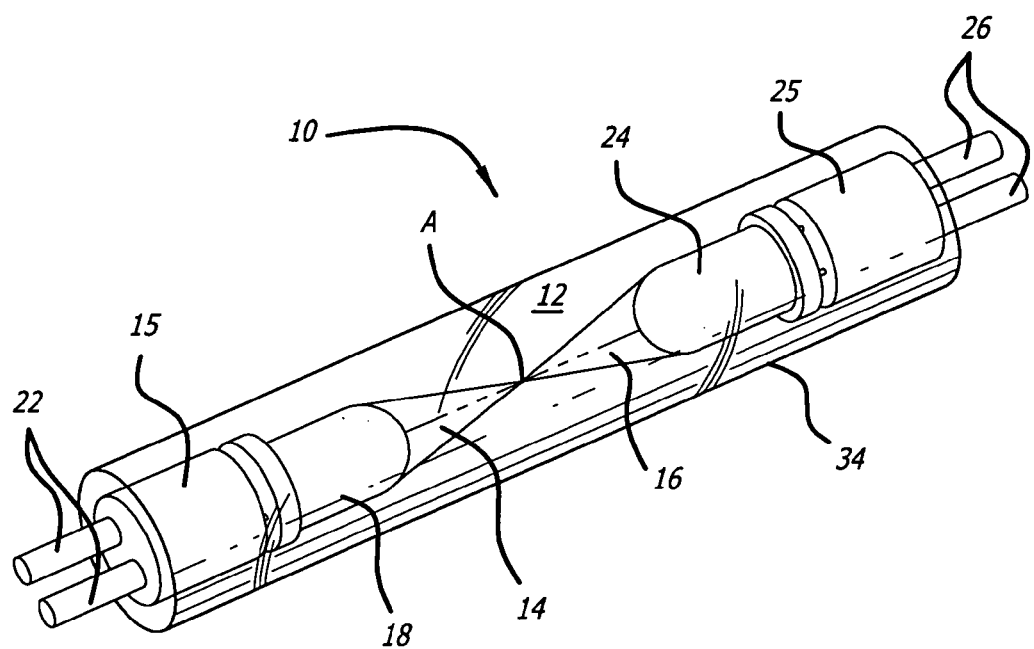
FIG. 2 is a perspective view of an axial section of the cylindrical body of the device of FIG. 1.
Figure 3:
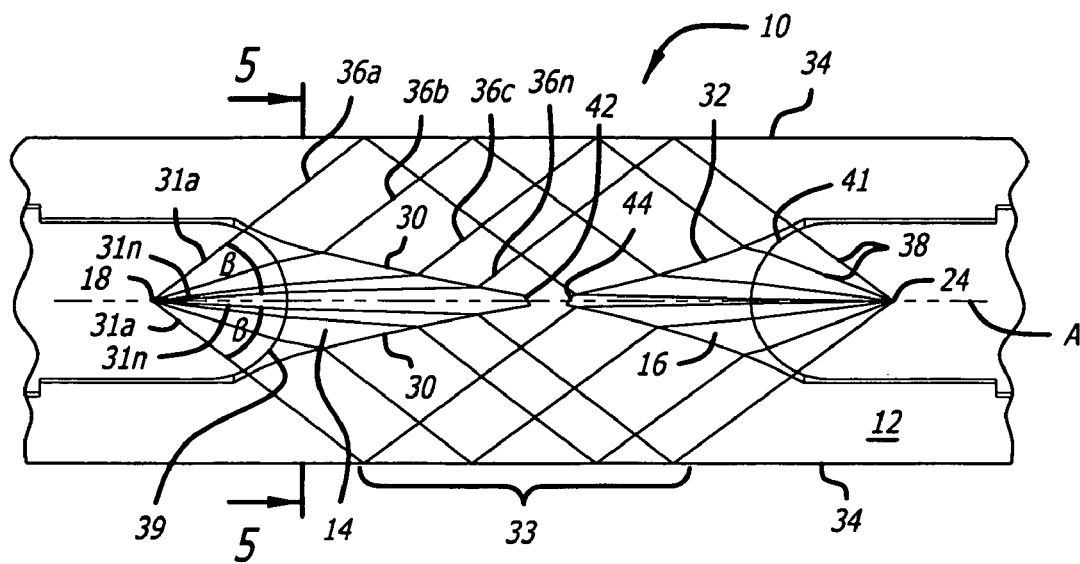
FIG. 3 is an enlarged schematic detail axial section of the body of the device of FIG. 1 showing the path of illumination rays within the useful illumination arc.
Figure 4:
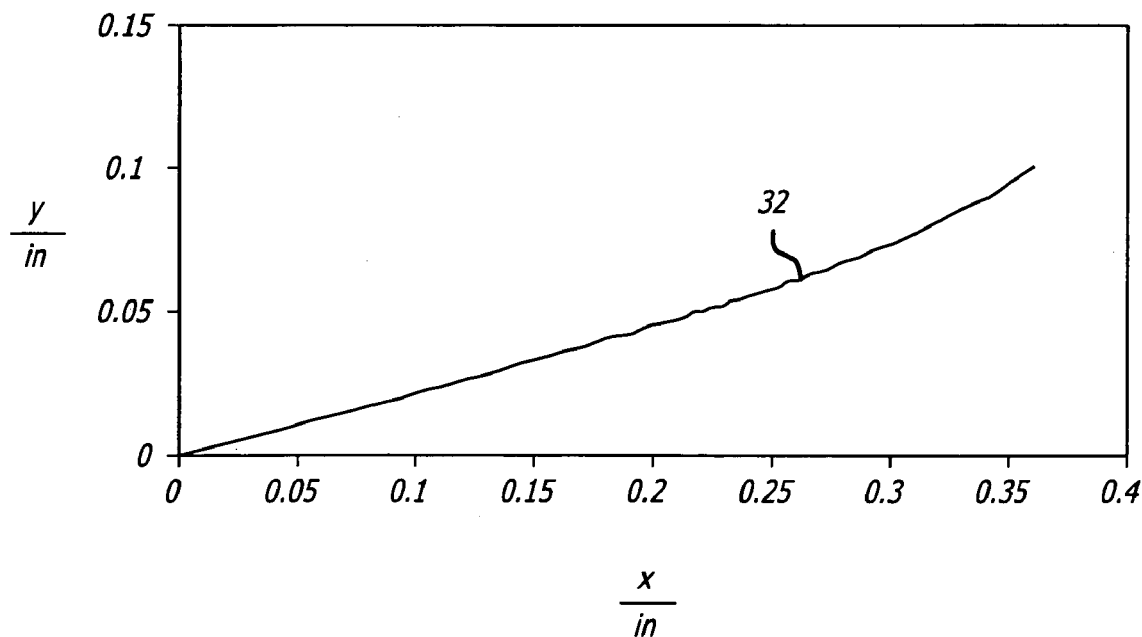
FIG. 4 is a graph of the shape computed by formula (1)
Figure 5:
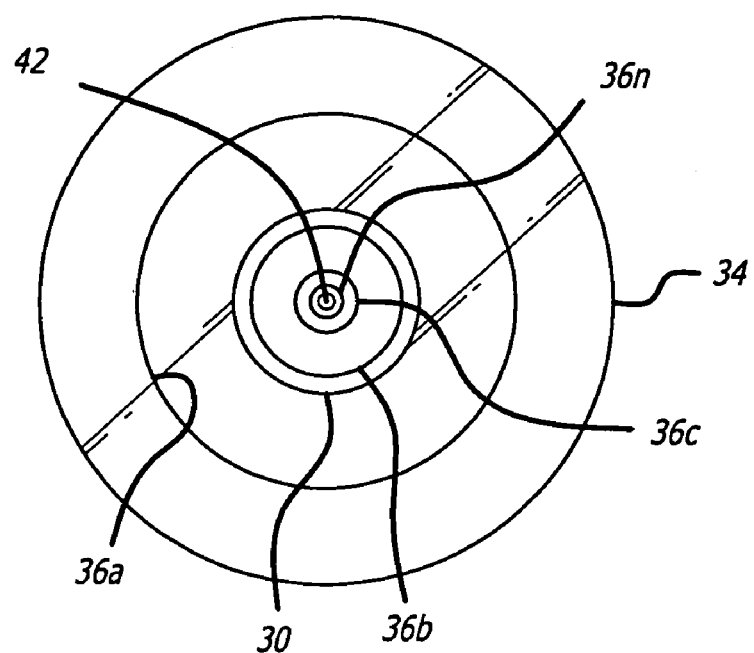
FIG. 5 is a transverse section of FIG. 3 along line 5—5.

FIGS. 2 through 4 illustrate in greater detail the inventive shape of the tapered walls 30, 32 of the cavities 14 and 16 that extend axially inwardly from the IRED 18 and phototransistor 24. As shown in FIGS. 3 and 4, the walls 30 and 32 are somewhat conical in appearance but are actually curved (in axial section) in accordance with formula (1) below. The effect of that curvature is that each ray (actually an element of a cone of optical energy, as demonstrated by FIG. 5) emanating from the IRED 18 between the limit rays 31a and 31n, in a given axial plane on each side of the axis A, is refracted at the air-COC interface of the wall 30 into parallelism with all other rays on the same side of the axis A, by virtue of Snell's Law.

A close examination of FIG. 3 will show that the rays emanating from the active element 37 of the IRED 18 are slightly refracted by the glass envelope 39 of the IRED 18. This refraction is, however, very small and can be essentially ignored in practice. Likewise, the infrared source of the IRED 18 is not exactly a point source but has some finite dimensions that can be ignored in practice. If a higher precision is desired, these factors can readily be taken into account by a MathCad design program.

Figure 6:
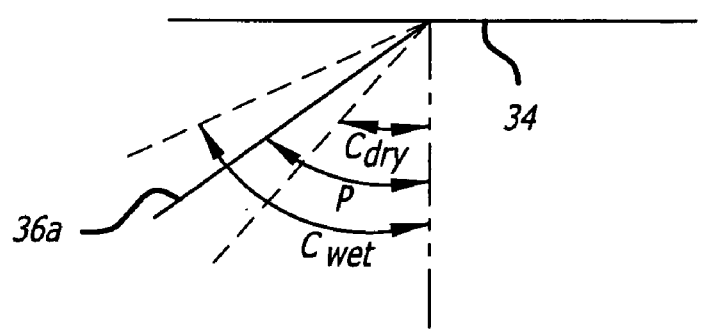
FIG. 6 is a diagram illustrating the parameters of internal reflection in the device of FIG. 3.

As shown in FIG. 6, the direction of the parallel rays 33 is such that the angle P at which they impinge upon the surface 34 of the cylinder 12 is half way between the critical angle $C_{dry}$ for a COC-air interface and the critical angle $C_{wet}$ for a COC-water interface at the cylinder surface 34.

As shown in FIG. 3, any rays internally reflected at the surface 34 are reflected toward the wall 32 of the phototransistor cavity 16. The wall 32 is curved in the same manner as the wall 30. Consequently, the parallel reflected rays 36a–n are refracted at the COC-air interface of wall 32 so as to become converging rays 38 that focus onto the phototransistor 24. The same considerations as listed above in connection with the glass envelope 41 and finite dimension of the phototransistor 24 apply here also.

When the cylinder surface 34 is dry or exposed to soil containing less moisture than is required to support vegetation, the critical angle $C_{dry}$ determined by Snell's Law for total internal reflection is less than the incidence angle P of the parallel rays 36a–n. Consequently, the rays 36a–n are totally reflected internally of the cylinder 12, and essentially all the energy emitted by the IRED 18 in the large useful arc β is collected by the phototransistor 24. The useful arc β is defined by the outermost ray 36a and the innermost ray 36n to reach the phototransistor 24.

As the water content of the soil increases as a result of irrigation, the critical angle C increases until it becomes equal to the incidence angle P. At that point, some of the infrared energy impinging upon the surface 34 is refracted outwardly of the cylinder 12 and is lost. The amount of refracted energy increases as the soil becomes wetter, until the soil's moisture content approaches saturation. At that point, a minimal amount of infrared energy is reflected toward the phototransistor 24. The effect of scatter by particulates in the ambient soil is essentially eliminated by the fact that only rays parallel to the internally reflected rays are focused onto the phototransistor 24.

The curvature of the walls 30 and 32 is defined for COC by the following equation (1):

$$\begin{pmatrix} Lp_i \\ x_i \\ y_i \end{pmatrix} := \begin{bmatrix} \sqrt{\left[L - \left(x_{i-1} + \frac{Lp_{i-1} \cdot \sin(\Delta\gamma) \cdot \cos(\alpha_i)}{\sin(\alpha_i \div \gamma_i \div \Delta\gamma)}\right)\right]^2 \div \left(\frac{Lp_{i-1} \cdot \sin(\Delta\gamma) \cdot \sin(\alpha_i)}{\sin(\alpha_i \div \gamma_i \div \Delta\gamma)}\right)^2} \\ x_{i-1} \div \frac{Lp_{i-1} \cdot \sin(\Delta\gamma) \cdot \cos(\alpha_i)}{\sin(\alpha_i + \gamma_i \div \Delta\gamma)} \\ y_{i-1} \div \frac{Lp_{i-1} \cdot \sin(\Delta\gamma) \cdot \sin(\alpha_i)}{\sin(\alpha_i + \gamma_i \div \Delta\gamma)} \end{bmatrix}$$

wherein L is the distance from the tip of the cone shape to the effective emission focal point for the LED (which lies on the axis); $L_p$ is the distance to the surface of the cone shape from the effective emission focal point for the LED for a given angle γ; the suffix i indicates a given point in a series of points defining the curve; γ is the angle subtended by the axis A and that line whose length is defined by $L_p$; α is the angle between the axis A and a line that is tangent to the conical surface in the cross section view that contains the axis A; and Δγ is the change in γ from point i–1 to point i. This results in the curve shown in FIG. 4.

It will be noted in FIG. 3 that the tips 42 and 44 of the cavities 14 and 16, respectively, are slanted. This prevents unreflected rays on or near the axis A from reaching the phototransistor 24, by refracting them away from the phototransistor 24.

Because the refraction characteristics of the walls 30 and 32 are sensitive to the presence of moisture in the cavities 14 and 16, the assembly and sealing of the sensor 10 is preferably performed in a dry nitrogen or other very low humidity atmosphere. This will prevent the condensation of any moisture in the air or gas trapped in the cavities 14, 16 when the sensor 10 is exposed to cold soils.

What is claimed is:

1. An optical moisture sensor, comprising:
  a) a solid, elongated body of transparent material having an axis, said body having formed therein first and second axially spaced cavities, each of said cavities being tapered in a direction toward the other;
  b) a light-emitting device positioned in said first cavity;
  c) a light-sensing device positioned in said second cavity;
  d) the walls of said first cavity being so curved that divergent light rays emanating from said light-emitting device are refracted at said first cavity walls into parallelism with each other in said material in a direction toward the surface of said body at an angle to said surface;
  e) the walls of said second cavity being so curved that parallel light rays impinging thereon from a direction toward said axis are refracted at said second cavity walls into convergence upon said light-sensing device;
  f) said angle being such that parallel light rays impinging upon said surface are substantially reflected as parallel rays toward said second cavity walls when said surface is exposed to a first fluid, and are substantially refracted outwardly of said body when said surface is exposed to a second fluid.

2. The sensor of claim 1, in which said body is cylindrical.

3. The sensor of claim 1, in which said first fluid is air and said second fluid is water.

4. The sensor of claim 1, in which said light-emitting device is substantially a point source of light.

5. The sensor of claim 1, in which said light is infrared.

6. The sensor of claim 1, in which said light-sensing device is a phototransistor.

7. The sensor of claim 1, in which said light-emitting device and said light-sensing device are positioned on said axis at the widest end of their respective cavities.

8. The sensor of claim 1, in which said material is highly resistant to moisture migration therethrough.

9. The sensor of claim 8, in which said material is a cyclic olefin polymer.

10. The sensor of claim 1, in which the tips of said cavities are so shaped as to refract substantially axial rays away from said light-sensing device.

\* \* \* \* \*